United States Patent
Hielscher et al.

(10) Patent No.: US 11,033,207 B2
(45) Date of Patent: *Jun. 15, 2021

(54) DYNAMIC OPTICAL TOMOGRAPHIC IMAGING DEVICES METHODS AND SYSTEMS

(71) Applicant: The Trustees of Columbia University in the City of New York, New York, NY (US)

(72) Inventors: Andreas H. Hielscher, Brooklyn, NY (US); Michael Khalil, Miami Lake, FL (US); Rajeev Dayal, Great Neck, NY (US); Inkyong Kim Parrack, Tampa, FL (US); Hyun K. Kim, Cresskill, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 78 days.

This patent is subject to a terminal disclaimer.

(21) Appl. No.: 16/216,137

(22) Filed: Dec. 11, 2018

(65) Prior Publication Data

US 2019/0282134 A1 Sep. 19, 2019

Related U.S. Application Data

(63) Continuation of application No. 15/294,086, filed on Oct. 14, 2016, now Pat. No. 10,178,967, which is a
(Continued)

(51) Int. Cl.
*A61B 5/00* (2006.01)
*A61B 5/1455* (2006.01)
(Continued)

(52) U.S. Cl.
CPC .......... *A61B 5/1455* (2013.01); *A61B 5/0053* (2013.01); *A61B 5/0066* (2013.01);
(Continued)

(58) Field of Classification Search
CPC . A61B 5/0066; A61B 5/02007; A61B 5/0073; A61B 5/0053
See application file for complete search history.

(56) References Cited

U.S. PATENT DOCUMENTS 3,010,452 A 11/1961 Smith
4,406,289 A 9/1983 Wesseling et al.
(Continued)

FOREIGN PATENT DOCUMENTS

JP 2001504718 A 4/2001
JP 2003527883 A 9/2003
(Continued)

OTHER PUBLICATIONS

European Search Report dated Mar. 13, 2014, in European Patent Application No. EP 11839420.
(Continued)

*Primary Examiner* — Joanne M Hoffman
(74) *Attorney, Agent, or Firm* — Potomac Law Group, PLLC

(57) ABSTRACT

The disclosed subject matter includes optical tomographic systems for acquiring and displaying dynamic data representing changes in a target tissue sample to external provocation. For example, the disclosed devices, methods and systems may be used for quantifying dynamic vascular changes caused by imposed blood pressure changes for diagnosing peripheral artery disease.

17 Claims, 8 Drawing Sheets

Related U.S. Application Data continuation of application No. 13/876,861, filed as application No. PCT/US2011/060489 on Nov. 11, 2011, now Pat. No. 9,492,089.

(60) Provisional application No. 61/412,717, filed on Nov. 11, 2010.

(51) Int. Cl.
*A61B 5/02* (2006.01)
*A61B 5/022* (2006.01)
*A61B 5/026* (2006.01)
*A61B 5/145* (2006.01)

(52) U.S. Cl.
CPC ............ *A61B 5/0073* (2013.01); *A61B 5/022* (2013.01); *A61B 5/02007* (2013.01); *A61B 5/0261* (2013.01); *A61B 5/14546* (2013.01)

(56) References Cited

U.S. PATENT DOCUMENTS

| | | | |
|---|---|---|---|
| 5,876,339 A | 3/1999 | Lemire | |
| 7,778,693 B2 | 8/2010 | Barbour et al. | |
| 9,492,089 B2 * | 11/2016 | Hielscher | A61B 5/02007 |
| 10,178,967 B2 * | 1/2019 | Hielscher | A61B 5/0066 |
| 2004/0039268 A1 | 2/2004 | Barbour et al. | |
| 2005/0243322 A1 | 11/2005 | Lasker et al. | |
| 2006/0018525 A1 | 1/2006 | Barbour | |
| 2006/0104859 A1 | 5/2006 | Tribelsky | |
| 2007/0232940 A1 | 10/2007 | Fine et al. | |
| 2008/0058622 A1 | 3/2008 | Baker | |
| 2008/0255471 A1 | 10/2008 | Naghavi et al. | |
| 2009/0079993 A1 | 3/2009 | Yatagai et al. | |
| 2010/0078576 A1 | 4/2010 | Ntziachristos et al. | |
| 2010/0152591 A1 | 6/2010 | Yu et al. | |
| 2010/0210931 A1 | 8/2010 | Cuccia et al. | |
| 2010/0262018 A1 | 10/2010 | Bakker et al. | |
| 2013/0289394 A1 | 10/2013 | Hielscher et al. | |

FOREIGN PATENT DOCUMENTS

| | | |
|---|---|---|
| JP | 20080538312 A | 10/2008 |
| WO | 1998017172 A2 | 4/1998 |
| WO | 2001020305 A1 | 3/2001 |
| WO | 2006111485 A2 | 10/2006 |
| WO | 2009157229 A1 | 12/2009 |

OTHER PUBLICATIONS

Flexman et al., "The design and characterization of a digital optical breast cancer imaging system," 30th Annual International IEEE EMBS Conference, Vancouver, British Columbia, Canada, Aug. 20-24, 2018, pp. 3735-3738.

International Search Report and Written Opinion for International Application No. PCT/US2011/060489.

Khalil et al., "Measuring peripheral vascular reactivity with diffusive optical imaging," Bioengineering Conference, Proceedings of the 2010 IEEE 36.sup.th Annual Northeast, IEEE, Piscataway, NJ, USA, Mar. 26, 2010, pp. 1-2.

Klose et al., Investigations of RA-Diagnostics applying Optical Tomography in frequency-domain, SPIE Proc. 3196, Optical and Imaging Techniques for Biomonitoring III, Jan. 13, 1998, pp. 194-205.

Lasker et al., "Digital-signal-processor-based dynamic imaging system for optical tomography", Review of Scientif Insturments 78, 083706 (2007).

Lasker et al., "Dynamic optical imaging of vascular and metabolic reactivity in rheumatoid joints," Journal of Biomedical Optics, Sep./Oct. 2007, vol. 12(5), pp. 052001-1-052001-13.

Office Action for Japanese Patent Application No. 2013-538958 dispatched on Oct. 31, 2017 (with English language translation).

Office Action for Japanese Patent Application No. 2013-538958 dated Jul. 11, 2016 (includes English language translation).

Office Action dated Apr. 14, 2015, in corresponding Chinese Patent Application No. 2011800537162.

Office Action dated Aug. 25, 2015, in corresponding Japanese Patent Application No. 2013-538958.

Office Action dated Jul. 27, 2015, in corresponding Chinese Patent Application No. 201180053716.2.

Office Action dated Mar. 16, 2017, in corresponding Korean Patent Application No. 10-2013-7014150.

* cited by examiner

DYNAMIC OPTICAL TOMOGRAPHIC IMAGING DEVICES METHODS AND SYSTEMS

CROSS-REFERENCE TO RELATED APPLICATIONS

This application is a continuation of U.S. patent application Ser. No. 15/294,086, filed Oct. 14, 2016, which is a continuation application of U.S. patent application Ser. No. 13/876,861 filed Jun. 18, 2013, now U.S. Pat. No. 9,492,089, issued on Nov. 15, 2016, which is a U.S. national stage filing under 35 U.S.C. § 371 of International Application No. PCT/US2011/060489 filed Nov. 11, 2011, which claims priority to and the benefit of U.S. Provisional Application No. 61/412,717 filed Nov. 11, 2010, the content of which are incorporated herein by reference in their entirety.

STATEMENT REGARDING FEDERALLY SPONSORED RESEARCH

This invention was made with government support under AR046255 awarded by the National Institutes of Health (NIH). The government has certain rights in the invention.

FIELD

The present disclosure relates generally to systems, devices, and methods for tomographic imaging, and more particularly to systems, devices and methods for tomographic imaging for peripheral arterial diseases.

BACKGROUND

Optical tomographic imaging uses signals from the amplitude attenuation or phase modification of light scattered by a tissue or sample. Injected light diffuses throughout a target and exits at the surface. Light can be injected and received at multiple positions on a surface of a target material, such as body structure, and the received light used to generate tomographic images. Amplitude attenuation and phase shift of the received light relative to can be used to resolve spatial information regarding the absorbing and scattering media in the target, for example, the spatial information can be presented in the form of a volumetric or cross-sectional image of the anatomy of a body part.

Peripheral Arterial Disease (PAD) is a highly prevalent atherosclerotic syndrome that affects approximately 8 to 12 million individuals in the United States and is associated with significant morbidity and mortality. PAD is responsible for approximately 275,000 hospital admissions per year, as well as over 2,750,000 office visits per year and approximately 45,000 deaths per year. PAD results from a variable combination of changes in the intima of arteries consisting of focal accumulation of lipids, complex carbohydrates, blood and blood products, fibrous tissue, calcium deposits. PAD also results from a build-up of plaque on the inside of the arterial walls, inhibiting proper blood supply to organs. The prevalence of PAD increases significantly with age. In a large study that included 5,450 patients, the prevalence of PAD based on the ankle-brachial index (ABI) increased from 9% of subjects 55-59 years of age to 57% of patients 85-89 years of age. The prevalence of PAD does not change with the patient's gender.

PAD typically manifests itself early in the legs and foot and is commonly referred to as lower extremity arterial disease (LEAD). Lower extremity arterial disease (LEAD) is defined as decreased arterial perfusion to the lower extremities. LEAD is a common condition in individuals with diabetes. LEAD in diabetes is compounded by the presence of peripheral neuropathy and by susceptibility to infection. Peripheral neuropathy causes a lack of sensation in the upper and lower peripheries leading to a patient's inability to feel cuts and bruises. Infections are thus more likely to occur.

If undetected, LEAD can progress to cause foot ulcerations, poor wound healing, gangrene, and ultimately amputation. Detection of LEAD is difficult, especially in patients with diabetes where calcification of the arteries and neuropathy alter the blood pressure measurements. The current techniques used to diagnose LEAD, such as the ankle-brachial index (ABI), typically use compressible arteries in order to accurately detect LEAD, complicating diagnosis in many patients. Currently the standard for identifying and treating occlusive LEAD in the arterial system is Digital Subtraction Angiography (DSA).

In DSA a contrast agent is injected intra-arterially to the patient and an image of the vasculature is obtained. However, this method of imaging is invasive and contrast media is nephrotoxic and therefore hazardous in patients with significant medical co-morbidities. In addition, the patient is exposed to ionizing radiation, which limits DSA's frequency of use. Peripheral vascular measures used to assess LEAD are usually derived from non-imaging techniques. Palpation of the peripheral pulses has been used as a clinical tool to assess occlusive LEAD in patients. However, the subjective nature of this method can lead to inconsistency amongst physician evaluations. Factors such as temperature, anatomical variation and the physician's palpation technique can greatly alter the diagnosis. Some physicians also use pressure cuffs to determine arterial blood pressure.

LEAD can also be assessed with invasive procedures. For example, the use of arterial catheters for blood pressure monitoring. Although these methods are sensitive and accurate, invasive methods tend to be more cumbersome to use, and they generally bear greater risk of adverse effects relative to non-invasive techniques. These factors alongside the higher cost, limit the use of invasive techniques as a screening tool.

Measurement of the ankle brachial index (ABI) which is the ratio of systolic pressure measured at the dorsalis pedis or posterior tibial artery to the brachial systolic pressure is also used to evaluate LEAD. However, the progression of LEAD in diabetes patients is frequently compounded by neuropathy and heavy calcification of the arteries that renders them non-compressible. Furthermore, blood pressure readings at the dorsalis pedis are often faint or in some cases absent. Pulse volume recordings (PVR) utilize blood pressure cuffs inflated to 60 mmHg and are placed at the thigh, calf, and forefoot level, and the volume of expansion and contraction of the extremity is measured in order to accurately gauge the amount of blood entering the extremity during the cardiac cycle. In the setting of arterial stenosis, PVR waveforms will be diminished and this measuring tool is used to complement ABI in patients with diabetes. However, PVR provides a more subjective rather than objective measure of the degree of arterial insufficiency.

LEAD can also be diagnosed using imaging methods such as velocimetry and continuous-wave Doppler ultrasound. The Doppler waveform obtained from a normal artery has a triphasic shape. However, measuring at an occluded location shows a waveform of increased velocity and bi- or monophasic behavior. Unlike ABI, and TSP, velocimetry only provides a qualitative measure of occlusive LEAD in compressible arteries. In addition, Doppler ultrasound cannot be used on patients with diabetes and non-compressible arteries because the pressures obtained in these patients are spuriously high. Due to the shortcomings of continuous wave Doppler ultrasound and ABI/PVR, Duplex Ultrasound is frequently used to analyze the peripheral vasculature. Duplex Ultrasound is a combination conventional B-mode ultrasound imaging with color Doppler and pulsed-wave Doppler waveform sampling. The limitations of duplex are that it fails to visualize up to 13% of arterial segments in the calf and is operator dependent.

Thus, while X-ray and MM provide great anatomical detail they typically do not provide enough physiological detail and smaller arteries may not be visualized or the artery may not have as much blood flow as expected.

SUMMARY

Optical tomography (OT) overcomes the limitations of current diagnostic techniques. The visible and near-infrared light used in the instrument typically has no adverse health effects and measurements can be repeated frequently. Furthermore, unlike X-ray angiography, which assesses blood vessel occlusion and obstructions in blood flow, OT allows assessment of the vessel. In addition, the OT imaging systems can use less expensive parts than X-ray instrumentation and can be scaled down to handheld portable systems. Therefore, OT imaging systems could be used at points of care as readily available screening devices.

Optical tomography can be used to detect the concentration of oxygenated and deoxygenated hemoglobin as well as the total hemoglobin concentration which is proportional to blood volume. These characteristics can be measured along with the absorption and scattering coefficients of the cross section being imaged. OT imaging is also independent of the compressibility of the arteries, and does not require the use of contrast agents to obtain valuable information about the blood content within the imaged body part.

Moreover, since optical tomography offers various kinds of contrast information (e.g., oxyhemoglobin and deoxyhemoglobin concentrations, blood volume, tissue-scattering) it can be further used to complement information obtained through other types of imaging modalities.

BRIEF DESCRIPTION OF THE DRAWINGS

The drawings described herein are for illustration purposes only and are not intended to limit the scope of the present disclosure in any way. The invention will be best understood by reading the ensuing specification in conjunction with the drawing figures, in which like elements are designated by like reference numerals. As used herein, various embodiments can mean some or all embodiments.

DETAILED DESCRIPTION

Embodiments of the present disclosure provide non-invasive optical tomography imaging modalities that can be used to detect and monitor peripheral arterial disease (PAD) in the lower extremities. The imaging of peripheral hemodynamics in the lower extremities can efficiently diagnose LEAD regardless of compressibility of the arteries, making it ideal for diabetic patients. Optical tomography can also be used to image vascular dynamics and blood flow patterns. Since in breast cancer and arthritis vascular changes are secondary effects, whereas in PAD changes in the vasculature are primary effects, the disclosed optical tomography imaging modalities can be used to diagnose and monitor vascular diseases. The breast imaging systems can be used to gather preliminary data on diabetic patients with PAD. Differences between healthy and diabetic PAD patients could be observed using these preliminary images.

Figure 1A:
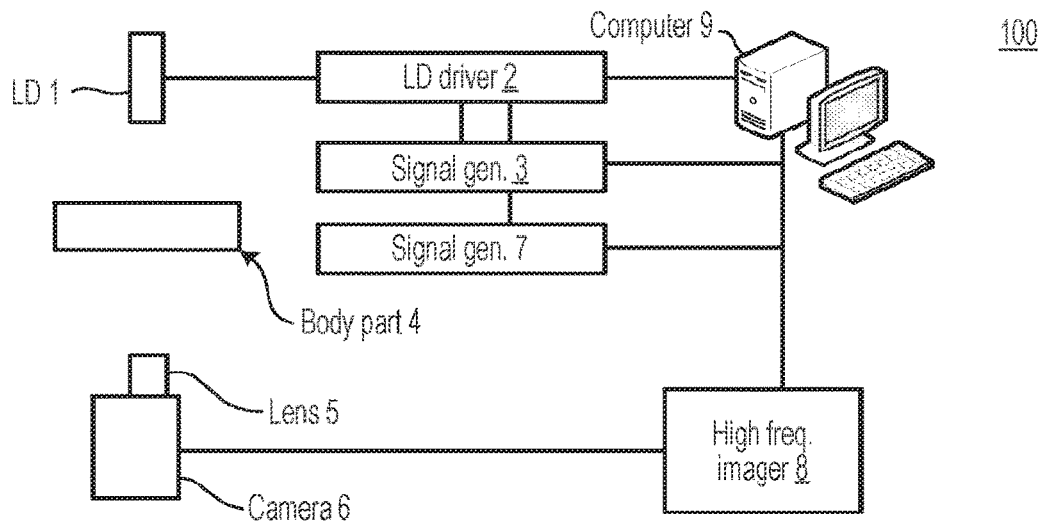
FIG. 1A shows a system for non-contact scanning of a target sample using a camera for imaging emerging light from a body part and a laser scanner for injecting photons into the body part. Although the example shown includes elements for frequency modulating the light source and can be used for frequency domain optical tomography, with minor changes, a similar arrangement is applicable to continuous wave or time resolves short pulsed optical tomography.

FIG. 1A illustrates an optical tomography imaging system 100 used in one embodiment. Frequency Domain Optical Tomography (FDOT) System: This frequency domain instrument is based on the Picostar HR imager (La Vision GmbH). The light sources consist of laser diodes (Picoquant GmbH) that are modulated by a signal generator (Aeroflex Intl. Ltd.) at frequencies up to 1 GHz. The laser light is coupled to an optical switch that demultiplexes the light into various optical fibers which deliver the light to different positions on an imaging geometry. Inside the imaging geometry resides the target to be imaged which will attenuate the light and induce a phase shift based on its optical properties. Detector optical fibers collect light exiting the imaging geometry and deliver the light to the Picostar imager. The detected light is incident on an image intensifier (Kentech Instruments Ltd.) that is also modulated by a signal generator at frequencies up to 1 GHz in order to demodulate the detected light. The demodulated detected light is measured by a CCD camera. By using a CCD camera, light can is measured in parallel from all detector fibers. By inducing phase shift between the modulating action of the laser and the demodulating action of the intensifier, one can use the measure light at the respective phase shifts in order to calculate the attenuation and phase shift induced by the imaged target. The measured attenuation and phase shift at several frequencies between DC and 1 GHz, is input to a frequency domain optical tomography reconstruction code in order to reconstruct the optical properties of the target. This system is currently being integrated with the MRI machine (see 5) to allow for simultaneous optical and MR imaging of small animals.

The system 100 can include a laser source LD 1, such as, but not limited to a laser diode, a laser diode driver 2, a signal generator 3 and 7, a body part (finger, foot, breast, etc.) placement area 4 for surface scan as well as transilluminating imaging, one or more lenses 5, an ICCD camera, a high frequency imager 8, and a computer processing system 9 to image body parts to produce cross section or volumetric images or raw transmission data. The data may relate, for example, to the volume or flow of blood through the major arteries of the body part, such as, feet, fingers, or other extremities. In operation, the body part 4 is scanned simultaneously with light from the laser diode LD1 and a second diode LD2 (not shown).

Both laser diodes can be mounted on the same or separate scanning mechanisms, such as a gear-wheel, for example, so that slight movements of the scanning mechanisms move the laser spot on the body part 4 to be imaged. In embodiments the laser may scan a line to acquire the surface geometry as explained below. Light from the same or a second diode LD1 may be transmitted through the body part 4 and the detected light intensity which is transmitted through the body part 4 captured by the camera 6. The background may serve as calibration of the camera coordinate system. The 3D surface coordinates are subsequently used to generate a 3D finite element mesh. This mesh together with the light transmission measurements from the light detectors are input to an image reconstruction algorithm that generates the cross-sections through the imaged body part.

Figure 1B:
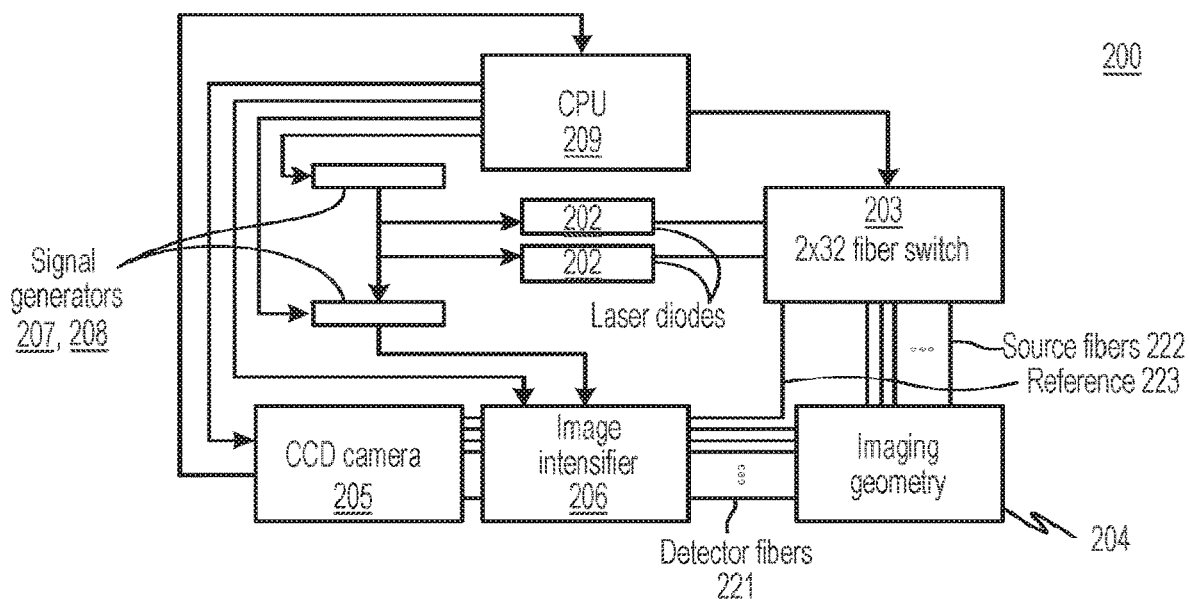
FIG. 1B shows another example of a frequency domain optical tomography system in which light is applied through a multiple optical fiber imaging system. The same configuration may also be used with continuous wave or time resolved short pulsed optical tomography.

FIG. 1B illustrates a frequency modulated optical tomographic system 200 that can also be used to generate tomographic images of a body part 4. The frequency modulated tomography system 200 includes two laser diodes 201, 202, generating light at two different wavelengths. Both laser diodes 201 and 202 are driven by modulated laser drivers and both are connected through optical fibers to a 2×32 fiber optic switch 203. Both source and detection fibers interface with the imaging geometry (e.g., measuring module) 204 in which the body part is placed. Detection fibers 221 that deliver light from the measuring module 204 have their respective tips of the fibers connected to the CCD camera 205. The camera images the fiber ends arrayed by the image intensifier 206. The image intensifier may or may not be used. Each laser diode 201 and 202 can be modulated at a different frequency by signal generators 207 and 208. The signal generators may be used to modulate the laser diodes 201, 202 as well as a photocathode of the image intensifier 206. The parameters of the generated signals (amplitude, frequency, phase, etc.) can be controlled by a computer processor CPU 209. The fiber optics switch 203 redirects the light from the two laser diodes 201, 202 in succession to the array of source optical fibers that deliver the light to fixed locations positioned around the measuring module. The light transmitted through the body part is carried by the detection optical fibers into the image intensifier 206. The source optical fibers 222 are optically coupled in pairs at different positions around the measuring module 204 to sample the body part at two different frequencies. A reference fiber 223 is also connected between the fiber switch 203 and the image intensifier 206. The signal from one of the signal generators 207 is input to both of the modulated laser diodes 201 and 202, whereas the input from the second signal generator is input only to the image intensifier 206. The frequency of the second signal generator 208 can be the same as the first signal generator 207 and the phase differences resulting between the two signals can be adjusted by the CPU 209. Using this set-up, the signals in respective pixels of the CCD depend on the phase difference. The source fibers serially illuminate the body part at discrete phase offsets.

Figure 1C:
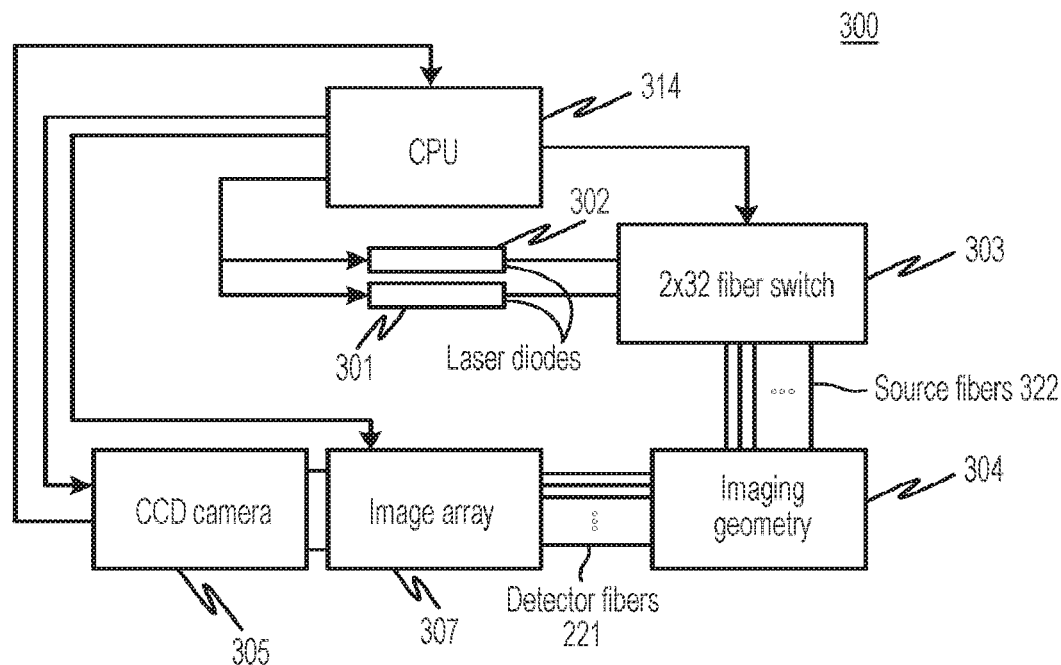
FIG. 1C shows a modification of the system of FIG. 1B for continuous wave optical tomography.

FIG. 1C illustrates a continuous wave tomography system 300 includes two laser diodes 301, 302, generating light at two different wavelengths. Both laser diodes 301, 302 are connected through optical fibers to a fiber optic switch 303. Both source and detection fibers interface with the imaging geometry (e.g., the measuring module) 304 in which the body part is placed. Detection fibers 321 that deliver light from the measuring module 304 have their respective tips of the fibers directed to the CCD camera 305 by the image array 307 which supports the fibers in known positions so their respective signals can be demultiplexed from the image of the camera. The parameters of the generated signals can be controlled by a computer processor CPU 314. The fiber optics switch 303 redirects the light from the two laser diodes 301, 302 in succession to the array of source optical fibers 322 that deliver the light to fixed locations positioned around the imaging geometry 304. The source optical fibers 322 are coupled in pairs at different positions around the imaging geometry 304 to sample the body part. The light transmitted through the body part is carried by the detection optical fibers to image array 307.

The imaging systems 100-300 can include various types of measuring module for bringing the illuminating light source such as a fiber into contact with the body part to be imaged (or projecting light onto the surface of a body part), and then bringing the detected light from the body part to the camera 6 or other photo detector. This may be accomplished with optical fibers, which either make direct contact with the body part, or are brought close to the body part in a simple, fixed geometry. In the case that the optical fibers do not make direct contact with the body part, an optical matching fluid (such as intralipid) may be used to direct the light from the fiber tip to the surface of the body part.

In order to create full 3D images of the entire imaged body part, the source optical fibers and the detection optical fibers that deliver and collect light from the entire body part are positioned around the body part, so that the tips of the source optical fibers and the tips of the detection optical fibers are adjacent to and are surrounding the body part. The light is effectively scanned over the body part by sequentially emitting light from one light source at the time and detecting the light intensity which is transmitted through the body part by the light detectors. One emitter may operate at a given time while all the receivers receive light scattered from the emitter. Then another emitter may be activated and so on. The light of different frequencies (color) may be injected simultaneously and demultiplexed to provide higher temporal resolution. Acquired or predicted 3D surface coordinates are used to generate a 3D finite element mesh. This mesh together with the light transmission measurements from the light detectors are input to an image reconstruction algorithm that generates the cross-sections through the imaged body part.

Figure 2:
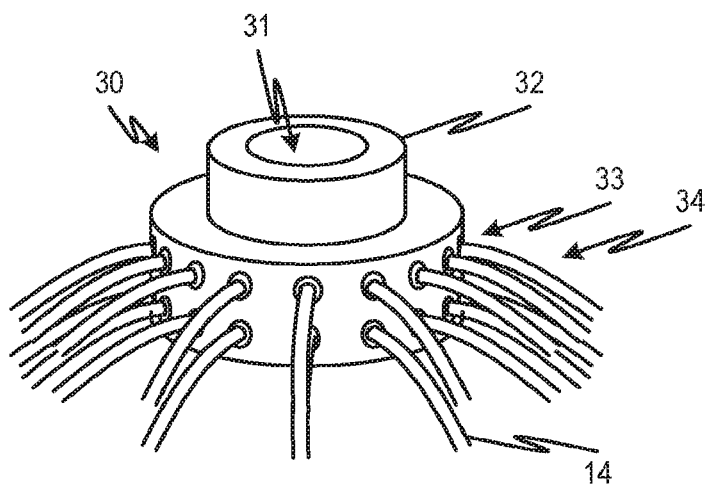
FIG. 2 shows an optical interface module that supports an array of optical fibers including both light emitters and receivers in contact or non-contact position to allow them to surround a body part such as a leg, arm, foot, finger, neck, or other body part to be investigated.

In the embodiment of FIG. 2, a measuring module 30 is used to image a finger 31 (not shown). The measuring module 30 includes a cylindrical body 32 into which the finger can comfortably slide and which acts to stabilize the finger throughout the imaging process. The measuring module 30 encircles a portion of the cylindrical body 32 so that the actual finger can be positioned inside the measuring module 30. A plurality of source and detection optical fibers 33 positioned in two separate rows are detachable attached to the measuring module 30 around the perimeter of the imaging module 30 Each row can include up to 24 optical fibers. The size of the measuring module 30 can be changed to accommodate fingers of various shapes and sizes. NIR light is delivered to the surface of the finger 31 through one fiber at the time (i.e., source optical fiber) and the transmitted light intensities are measured by all other optical fibers (i.e., detection optical fibers). The captured transmission data is delivered to the photodetector for further processing. Using image reconstruction software, the detected transmitted light data can be used to generate three-dimensional cross sectional images of the body part.

Figure 3:
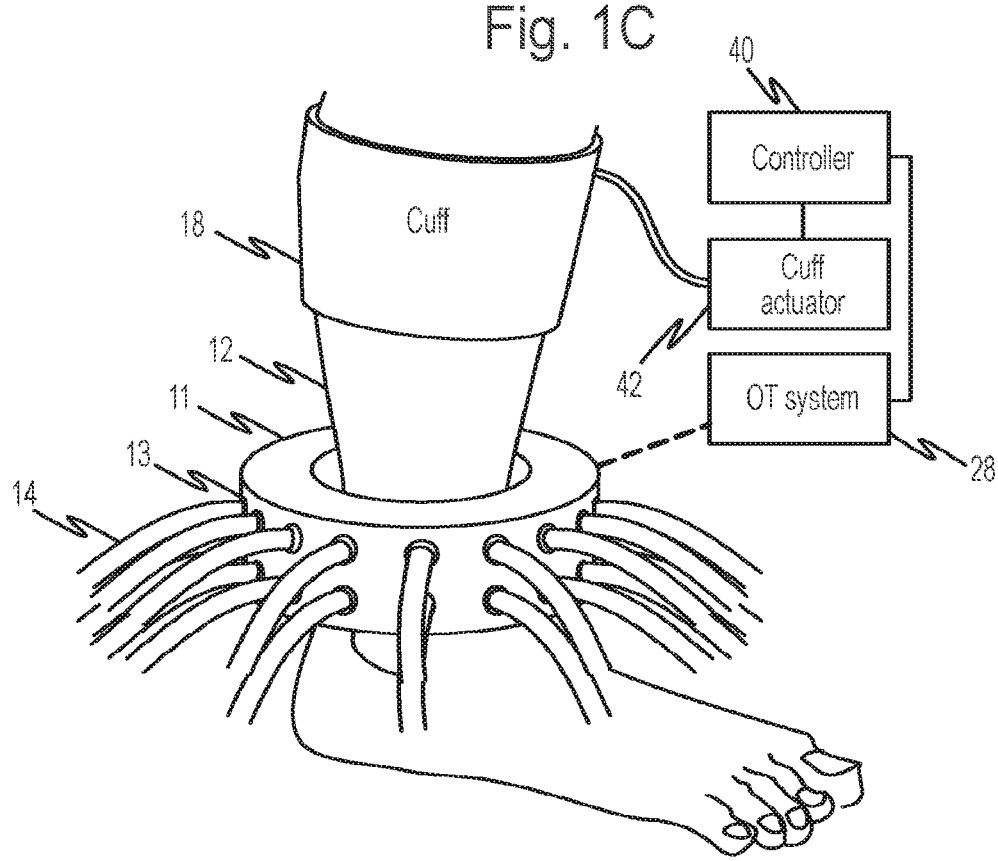
FIG. 3 shows the optical interface module of FIG. 2, sized for and arranged in position about a human ankle.

A measuring module 11 is shown in FIG. 3. In this embodiment, the body part that is being imaged is the lower part of a leg 20. The measuring module 11 can be a cuff-shaped device that rises a few inches above the ankle and is configured to accommodate various leg 20 sizes while still keeping the relative source-detector fiber 13 positions constant. The measuring module 11 includes a plurality of source optical fibers 13 and detection optical fibers 13 detachably attached to the cuff-like device and arranged in at least two layers around the cuff-like device 11 so as to encircle the lower part of the leg 12 and so that when in use, the source and detector fibers 13 deliver near-infrared (NIR) light to the major arteries of the leg 12, and deliver the light transmitted through the major arteries of the leg 12 to the photodetector.

Each source and detector fiber 13 can be connected to a light conduit 14 to deliver light from the laser source of an optical tomography systems 28, which could be any one of systems 100-300, for example, to the body part 12 and to deliver transmitted light from the body part 12 to the photodetector of the optical tomography system 28, which can be any one of the optical tomography systems 100-300. The measuring module 11 is configured to be variable in size so that any size leg 12 can be comfortably fitted inside the measuring module 11.

The measuring module 11 can target the response around the dorsalis pedis artery, the response of the posterior tibial artery, as well as the response across the calf to measure the perfusion at an elevated location on the lower extremities. The source optical fibers and the detection optical fibers in the measuring module 11 can be positioned so as to surround a major artery of the lower leg 12. In operation, after the patient places a leg 12 inside the measuring module 11, the module 11 can be filled with a matching liquid to overcome the gap between the foot 12 and the source and detection optical fibers 13. The matching liquid can help to overcome mismatches between the measuring module 11, and the leg 12 being imaged.

Visible and near-infrared (NIR) light is guided through the optical fiber conduits 14 to the surface of the leg 12 under investigation. Each of the source optical fibers 13 sequentially delivers light to the major arteries in the leg 12 while each of the detection optical fibers 13 capture the light transmitted through the arteries at various locations. The specific geometry between the source optical fibers and the detection optical fibers allows the detection optical fibers to capture reflected and transmitted light through the major arteries of the leg 12. The captured transmission data is then delivered to the photodetector for further processing.

Using image reconstruction software, the detected transmitted light data can be used to generate three-dimensional cross sectional images of the body part. In order to determine whether there are any changes in the vasculature of the body part imaged or in the oxy and deoxy-hemoglobin or in the main protein in blood, a second set of transmission data and corresponding second set of images are generated after an external stimulus is applied to the imaged body part. The stimulus can be generated by applying an external pressure on the body part using a pressurizing device, such as but not limited to, a sphygmomanometer cuff 18 placed around the body part 12.

After the application of the stimulus, a second set of transmission data are taken and a second set of tomographic images are reconstructed using the same imaging and reconstruction methods as used for the generating of the first set of data and images. The cuff 18 is activated to exert pressure on the leg 12 by a cuff actuator 42. The amount of pressure exerted by the cuff 18, as well as the timing of sequential release of pressure is controlled by a controller 40. The controller is operatively connected to the cuff actuator 42 as well as the system 28.

Each set of transmission data and reconstructed images include information regarding optical properties (reflection, absorption, scattering) of the imaged body part. From these optical properties, parameters such as perfusion rates, oxy and deoxy hemoglobin concentrations, as well as blood volume can also be determined. By comparing the transmission data and the images in the first set with corresponding transmission data and images in the second set, biomarkers such as, but not limited to, distribution of optical properties, perfusion rates, and differences in oxy and deoxy hemoglobin concentrations can be ascertained. These biomarkers can then be used to differentiate between a sick and a healthy patient. The optical tomography system 28 may have a controller 40 which operates the cuff and OT system to perform an end to end diagnostic sequence.

Figure 4:
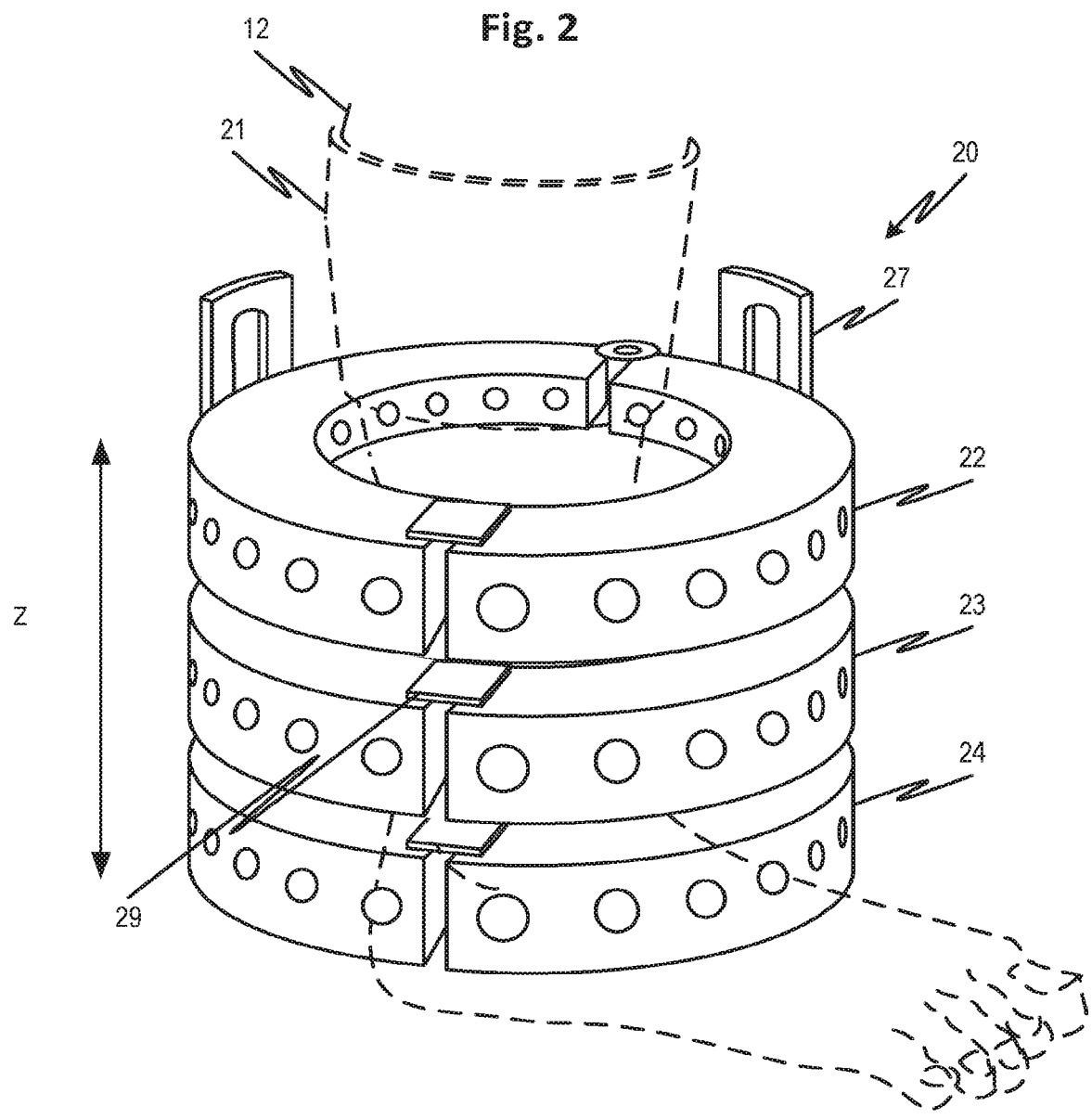
FIG. 4 shows an optical interface module that can be opened as a clamshell and which permits an axial spacing of respective ranks of optical fibers to be adjusted.

In the embodiment of FIG. 4, a cuff-like measuring module 20 is shown. The cuff-like measuring module 20 can include a plurality (three shown) of adjustable rings 22-24, each including a plurality of source optical fibers and detection optical fibers positioned around a surface of the ring. The cuff-like measuring module 20 is adjustable in diameter in order to accommodate various leg sizes and can open similar to a handcuff for easy attachment and detachment. Each of the rings includes two separate parts linked together using bracket type connecting members 27, which when positioned in a first locked position, securely lock the rings 22-24 together, and when in a second unlocked position, the rings may be moved in the axial (Z axis) direction relative to each other to change the mutual spacing of the rings. The rings can also be opened by means of a clasp 29. The brackets may include a plurality of engaging surfaces, to act as stops, positioned along the length of the brackets 27 to allow the rings to be securely positioned in different positions along the length of the bracket when in the desired position. The rings 22-24 are detachably attached to the brackets 22 to render a boot-like device 20. Each ring 22-24 can be placed strategically around the lower extremity of the leg 12 to encircle the major arteries in the desired portion of the leg 12. The width of the measuring module 20 as well as the measuring rings 22-24 can be adjusted to accommodate different leg sizes. The rings 22-24 can be placed around the metatarsals and the ankle as well as the calf to obtain the hemodynamic response in the major arteries and its surroundings and that of a higher portion of the lower extremity. The rings 22-24 can also move in a vertical direction Z so as to be able to be positioned at any desired height on the measuring module 20 and around the body part 12. The rings 22-24 with the optical fibers distributed around the ring detect the transmission and reflectance of light through the arteries of the leg 12.

This design may employ an optical spacer but may also instead allow the optical fibers to make direct contact with the skin and still maintain constant source-detector fiber positions. In case the design does not have a constant geometry, a robust image reconstruction technique called the Normalized Differentiation Method (NDM) can be used to reconstruct the images. This reconstruction algorithm can take the difference between a baseline optical measurement and the optical response measurement relative to a stimulus. This method can reconstruct the difference/relative optical properties instead of absolute optical properties and is therefore not nearly as dependent on the boundary conditions and the source detector optical fiber positions.

The measuring modules 11 and 20 can target the response around the dorsalis pedis artery, the response of the posterior tibial artery, as well as the response across the calf to measure the perfusion at an elevated location on the lower extremities. The source optical fibers and the detection optical fibers in both measuring modules 11 and 20 can be positioned so as to surround a major artery of the lower leg 12.

In operation, after the patient places a leg 12 inside the boot 11 or 20, the boot can be filled with a matching liquid to overcome the gap between the foot 12 and the source and detection optical fibers 13. The matching liquid can help to overcome mismatches between the measuring module 11, 20, and the leg 12 being imaged. Visible and near-infrared (NIR) light is guided through the optical fiber conduits 14 to the surface of the leg 12 under investigation. Each of the source optical fibers 13 sequentially delivers light to the major arteries in the leg 12 while each of the detection optical fibers 13 capture the light transmitted through the arteries at various locations. The specific geometry between the source optical fibers and the detection optical fibers allows the detection optical fibers to capture reflected and transmitted light through the major arteries of the leg 12. The captured transmission data is then delivered to the photodetector for further processing. Using image reconstruction software, the detected transmitted light data can be used to generate three-dimensional cross sectional images of the body part.

The constant geometry of the source fibers and detection fibers around the measuring modules may facilitate reconstruction of these optical images, because of the precise locations of the source and detection fibers are known along the boundaries of the measuring modules 11 and 30. Various reconstruction algorithms can be used to generate the images, such as, but not limited to model based iterative image reconstruction algorithms, diffusion-based algorithms, and transport theory reconstruction algorithms.

Figure 5:
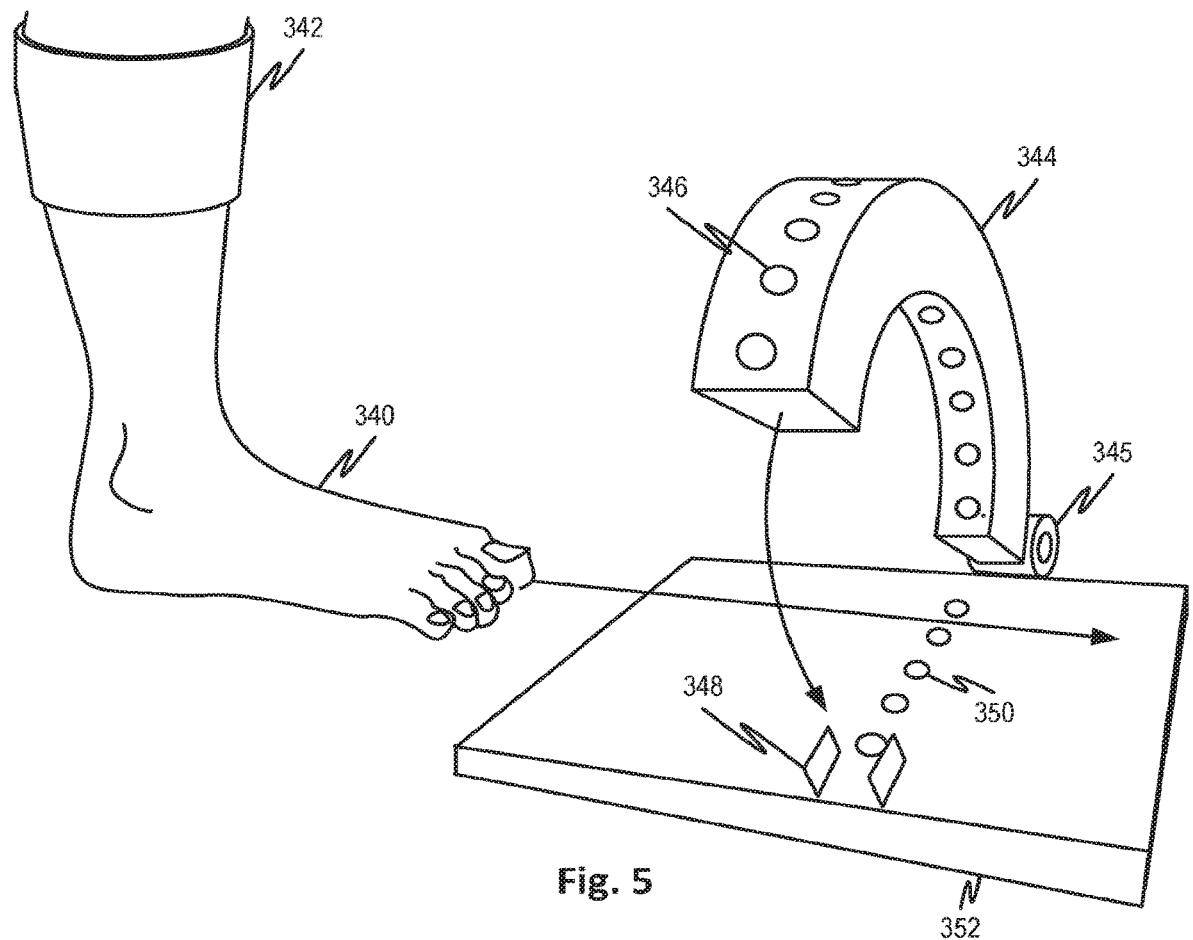
FIG. 5 shows an optical interface module that can be opened and closed about a foot, for example the metatarsal region thereof, with a flat portion and an arching portion. The fiber supports may support fibers for contact or non-contact arrangement over the body part.

FIG. 5 shows an optical interface module that can be opened and closed about a foot 340, for example the metatarsal region thereof, with a flat portion 352, which acts as a base upon which the patient can stand. The optical interface modules also have an arching portion 344. Both the base 352 and arching portion 344 support fibers (locations thereof indicated at 346 and 350) for transmitting and receiving light signals. The fiber supports may support fibers for contact or non-contact arrangement over the body part. The arching portion may be attached by a hinge 345 to allow the arching portion 344 to be positioned over the foot. A latch 348 to hold the arching portion 344 firmly, once closed, may be provided. A cuff 342 may be provided for provoking the vasculature of the foot.

Figure 6:
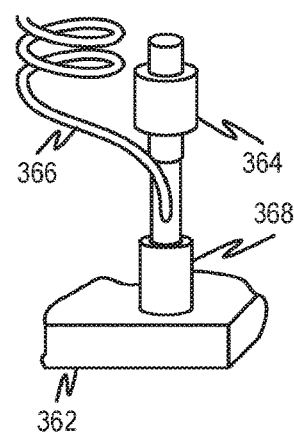
FIG. 6 shows a single fiber support and an associated linear actuator configured to move the end of the fiber to known position in contact or non-contact relation to a body part. The feature of FIG. 6 is applicable to any of the embodiments disclosed.

FIG. 6 shows a single fiber support 362, 368 and an associated linear actuator 364 configured to move the end of the fiber 366 to known position in contact or non-contact relation to a body part. The feature of FIG. 6 is applicable to any of the embodiments disclosed. A controller as in any of the embodiments described herein may be used to position each of the fiber ends to a desired position automatically based on acquired or predicted surface geometry as described elsewhere herein. By knowing the precise position of the actuator and the support, the position of the fiber end may be known. Even if the fiber end, in contact with the skin, obscures the body part, the shape of the anatomy may be inferred by knowing the precise position of the fiber end if it is assumed the skin conforms to it. Such actuators may be provided, for example, in the apparatus of FIG. 5 or any others compatible devices.

In alternative embodiments, the linear actuator may be replaced by a movable support with a spring that permits the light guide to move passively therewithin. The support may further include an encoder to indicate a position of the light guide relative to the support. The information from the encoder may be used to form the mesh.

Figure 7:
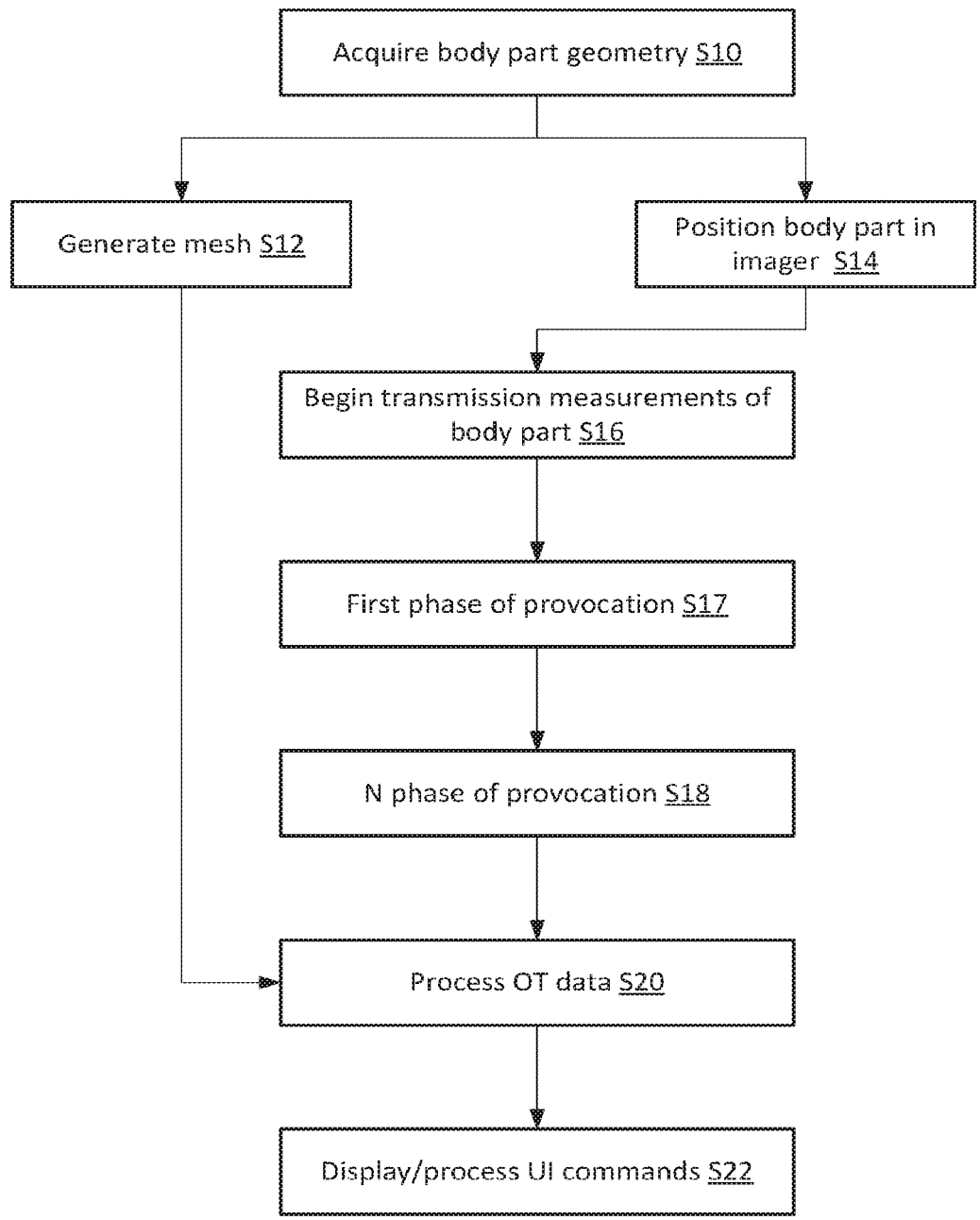
FIG. 7 shows a method for scanning a body part including the control of the provocation of the body part (e.g. pressurizing the vasculature therewithin), and the acquisition of time series data, as well as the generation of image data and interactive display thereof.
Figure 10:
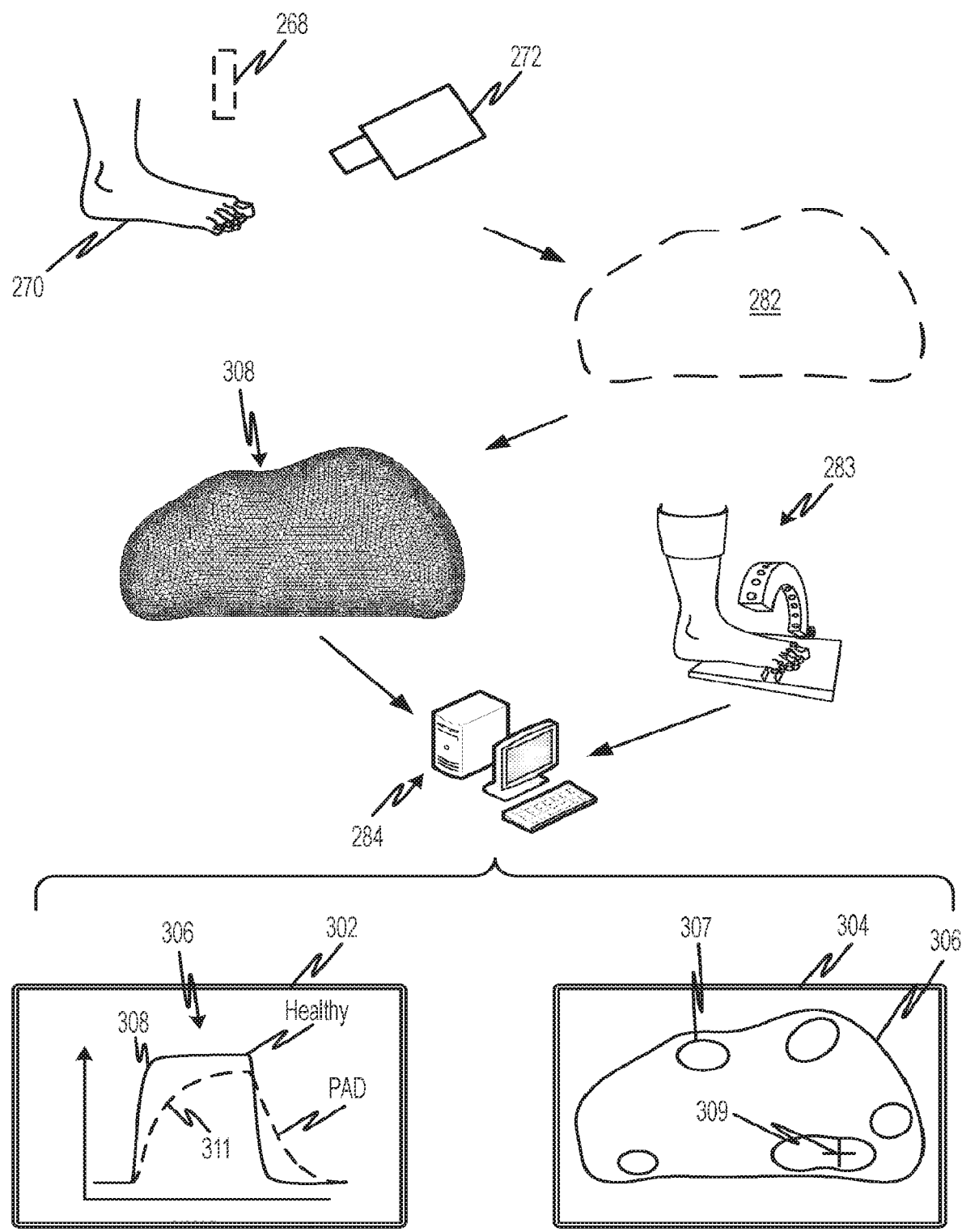
FIG. 10 illustrates a process and system for acquiring image data and presenting the same to a user.

Referring now to FIGS. 7 and 10, in a relevant embodiment, at S10 a body part such as a foot is surface scanned, imaged (photographed from multiple angles, for example) to derive raw data from which a 3 surface model can be generated. Alternatively a predicted surface is used, for example, by drawing from a library of stored template for different anatomical archetypes.

To obtain the geometry for image reconstructions, a photograph of the foot or a laser scan surface geometry acquisition system may be used. Adjacent objects may be provided to give a reference to obtain precise absolute dimensional data. The surface geometry information may be used to create a boundary and locate the sources and detectors. In embodiments in which one or more actuators position the fiber ends into known positions in contact with the body part, the known positions and sizes of the fiber ends are used in determining the surface geometry. The process is illustrated figuratively in FIG. 10 where a camera 272 images a foot 270 which is scanned by a laser 268 to acquire the surface geometry indicated at 282.

At S14 the body part is positioned in the imaging device (283 of FIG. 10). Alternatively, the body part may already be positioned in the imaging device if concurrent surface geometry acquisition is done while positioned therein. The latter may be the case where a device such as non-contact imaging is done or where the positions of the fibers in contact with the body can be obtained directly such as with the actuator of FIG. 6.

Optical transmission measurements on the body part, such as the foot, are begun at S16. In embodiments, these may be performed with a digital near-infrared optical tomography imager. In that case, a combined optical beam consisting of two laser diodes (wavelength λ, =765 nm and 830 nm) may act as illuminating sources. The sources may be sequentially coupled into different 1 mm multimode fiber bundles that distribute light to multiple areas along the measurement probe. The measurement probe may have any number of fiber supports that hold optical fibers close to or in contact with the surface of the body part such as a foot. For example, the device of FIG. 5 may be used.

The current of each laser diode may be modulated to a distinct amplitude and frequency. In this way, multiple wavelengths may be illuminated simultaneously, and their respective amplitude and phase contribution on the attenuated detected signal can be extracted using synchronous detection techniques. The total power incident on the target may be, for example, about 30 mW. Once the light is attenuated as it propagates through the body part, it then exits the probe and is collected by the various fiber bundles positioned around the target for a fiber multiplexing scheme. As described here and elsewhere other schemes for optical tomography transmission measurements are also possible, for example, non-contact using imaging as in FIG. 1, without the use of fiber multiplexing. In an exemplary embodiment, a total of 34 fibers may be brought in contact with the foot with 14 serving as light sources and 20 as detection fibers.

At S12, in parallel or series with other steps, a mesh may be generated using the data from the surface geometry 282 and or a priori information of anatomy (or patient-specific documentation such as medical imaging studies). For example, a two dimensional mesh of a foot (FIG. 10, 308) may be generated. Alternatively a three-dimension mesh may be generated.

At S17, a provocation is induced in the body part. For example, the flow through the vasculature may be modified using a pressure cuff that is applied proximally of the imaging module, for example, to the upper thigh. Initially, a baseline measurement may be taken, for example, for an interval of approximately 1 minute and data recorded for the generation of multiple image frames, for example, 400 frames. Next, the pressure cuff may be inflated to a first pressure, for example to produce a venous occlusion (for example, 60 mmHg)/The pressure may be maintained for an interval while data is acquired continuously (for example, 1.5 minutes) at which point the pressure may be released to generate a rest interval during which data is also recorded. As indicated at S18, a number of additional provocations may be induced with continuous data acquisition for the generation of time series imaging (or non-imaging) data during each and in the interval between. For example, an increased pressure of 120 mmHg for arterial occlusion may be applied to a proximal cuff with a following rest period, the intervals being the same as for the venous occlusion. The provocations may be repeated multiple times, for example three times, to confirm repeatability, for statistical analysis or for merging data for random error filtering.

At S20 the data are processed by system (FIG. 10, 284) for display. For example, to generate two-dimensional reconstructions of the optical properties of a body part such as the foot, a transport-theory-based PDE-constrained multispectral image reconstruction scheme may be used to reconstruct the spatial distributions of the oxy and deoxy-hemoglobin concentrations in the foot. For this purpose, the differences in Hlb021 and [Hb] obtained through reconstruction is relative to baseline which may be assumed to be given by Hlb021=23.4306 μM1 and [Hb]=14.6874 μM1, throughout the body part. A radial basis function (RBF)-type regularization scheme may be employed to obtain quality images by reducing noise and artifacts near the foot surface.

Figure 8A:
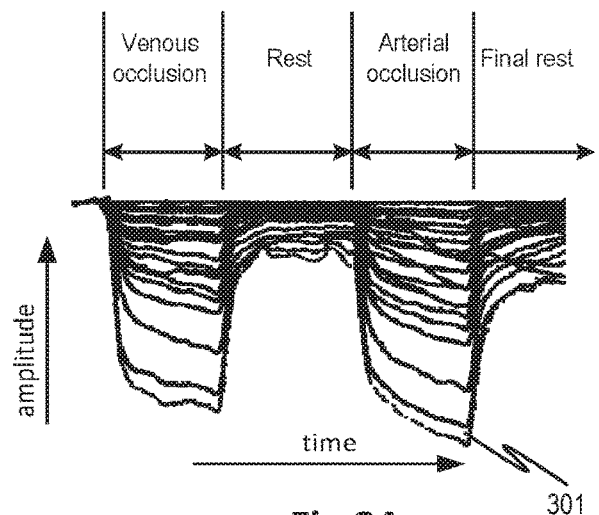
FIGS. 8A through 9B show the temporal response of multiple detector intensities at the finger and foot for a healthy person and a diabetic person with peripheral vascular disease. The traces depict the transmission profile over select detector channels for a single illumination position at one wavelength each. The responses are plotted as a change in intensity versus time (minutes) and are normalized to a rest period prior to provocation of the vasculature.
Figure 8B:
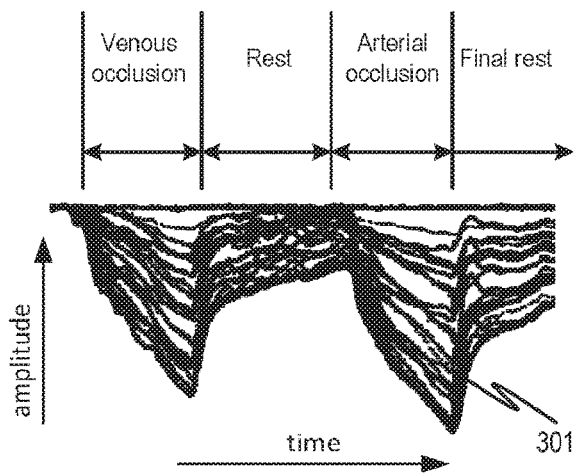
Figure 9A:
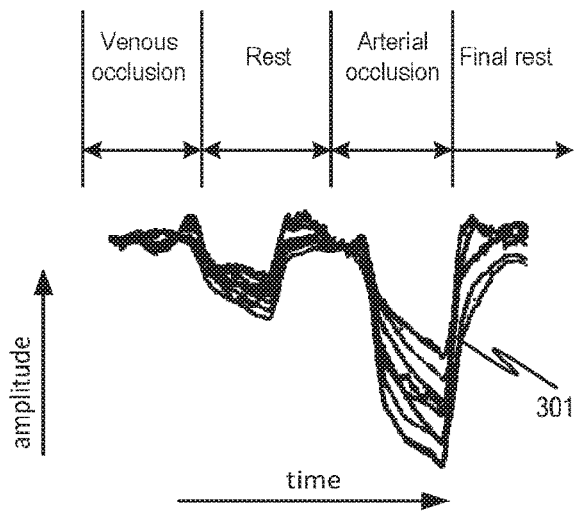
Figure 9B:
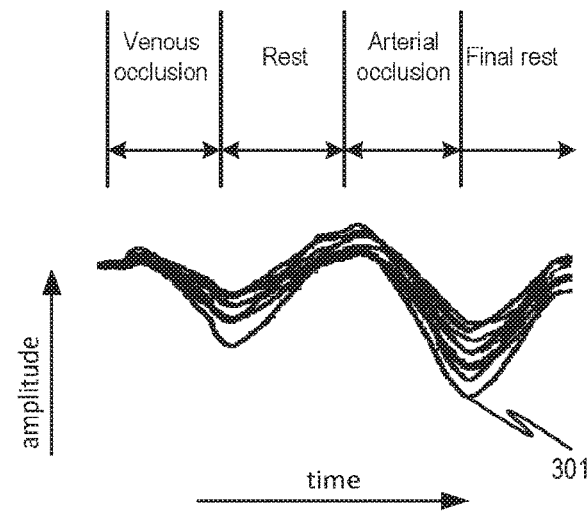

In an actual example, the observed signal changes corresponded to understandable physiologic responses in a foot and finger. FIGS. 8A through 9B show the temporal response of multiple detector intensities at the finger (FIGS. 8A and 8B) and foot (FIGS. 9A and 9B) for a healthy person (FIGS. 8A and 9A) and a diabetic person with peripheral vascular disease (FIGS. 8B and 9B). The traces 301 depict the transmission profiles over respective detector channels for a single illumination position at one wavelength each. The responses are plotted as a change in intensity versus time (minutes) and are normalized to a rest period prior to provocation of the vasculature. When the first pressure cuff (@ 60 mmHg) is applied to a healthy volunteer, venous return is inhibited while arterial supply is still active, causing blood to pool in the leg. As a result, the optical attenuation absorption increases causing a decline in transmitted intensities. Subsequent to the pressure being released, the accumulated blood volume begins to diminish, at first rapidly, due to the elevated pressure gradient in the vascular system, and then more gradually as the gradient eases toward equilibrium and the optical signal returns towards baseline. When the cuff is reapplied (e.g., at 120 mmHg) the signal magnitude drops even further relative to the initial value, indicating a more complete venous occlusion. The time traces of patients with PAD show significantly different behaviors from those of a healthy volunteer. While in all the cases a drop in transmitted intensities is observed upon application of the pressure cuff, the drops of the PAD patients are much smaller in magnitude (15%) than the healthy volunteer. In addition, in both PAD cases the occlusion and recovery rate appear to be almost linear, however the healthy volunteer's rates show a more exponential profile.

In an example embodiment, the transmission and surface data may be processed to reconstruct and display 304 a section view 306 of the body part in which the concentration or volumes of interest are suitably highlighted 307. For example, the HbT concentrations in the arteries of the foot may be shown with a color or luminance channel indicating the amount or properties of blood (e.g., oxygenation). In an embodiment, the display interface may permit the selection of a particular part (e.g., a pixel) for which selected part the time trace of the target property may be displayed as indicated at 306 in display 302. For example, a cursor 309 may be provided for this purpose. A reference 308 trace (healthy) may be superimposed on the measured trace 311 (PAD) for comparison. The reference trace may be selected from a library and may represent statistics of classes of pathology or other groups.

The finger results above are from a study in which an arm cuff was used to provoke the finger vasculature. Actual observations by the inventors show that the ankle brachial index (ABI) can easily distinguish between the healthy subjects and PAD patient but in some cases the differences are not clear. A healthy volunteer and a patient with both diabetes and PAD can have very similar ABI measurements. Yet the optical transmission traces clearly show a compromised vasculature in the observed cases, indicating that optical methods may provide a more reliable test for PAD in patients with diabetes than ABI.

Model based iterative algorithms (MOBIR) typically include three elements, such as a forward model, an objective function, and an updating scheme The forward model can give a numerical solution of the light distribution inside the object Ω and predicts the measurements (energy radiance $\Psi_d$) on the boundary ∂Ω. To predict these measurement one can provide the source strength $S(r_s)$, the source positions $r_s$ and an initial guess of the optical biomarkers $\mu_0 = [\mu_{s,0}(r), \mu_{a,0}(r)]$. A given set of measurements M on the boundary ∂Ω can then be compared with the set of the predicted radiances $\Psi_d(\mu_0)$ by defining an objective function Φ. A simple example can include the least square error norm between measured and predicted data given by $$\Phi = \sum_s \sum_d (M_{s,d} - \Psi_{s,d}(\mu))^2 / \sigma^2 \qquad (1)$$

An updating scheme can be employed that provides a new guess of optical biomarkers $\mu_0 + \Delta\mu$, which reduce the value of the objective function Φ. A new forward calculation can be performed based on the new set of optical biomarkers $\mu_0 + \Delta\mu$. The iteration process can be finished when the minimum of the objective function is reached within a specified error. At this point the predicted detector readings can be identical to the measured detector readings within a given tolerance. The optical biomarkers, can be mapped into a two or three-dimensional image.

Algorithms differ in the way updates are obtained, how the objective function is defined and what forward model is used. While changing the updating scheme can affect the convergence speed of a code, changing the objective function or the forward model can affect the accuracy of the reconstruction result. As a forward model most groups use the diffusion equation given by $$\left(\frac{1}{c}\frac{\partial}{\partial t} + \mu_a(r) - \nabla(D(r)\nabla)\right)\phi(r,t) = S(r,t). \qquad (2)$$

Using finite-difference, finite-element, or analytical solution, predictions of the fluence (energy per unit area) on the surface of the medium are made.

The diffusion based algorithm can be an approximation of the more generally applicable integro-differential equation of radiative transfer (ERT), given by $$\Omega\nabla\Psi(r,\Omega) + (\mu_a + \mu_s)\Psi(r,\Omega) = S(r,\Omega) + \mu_s \int_{4\pi} p(\Omega,\Omega')\Psi(r,\Omega')d\Omega'. \qquad (3)$$

In cases where the diffusion approximation is not valid, using this approximation can lead to erroneous prediction of the measurements.

Diffusion-based calculations can predict an almost constant fluence rate in the area of the fluid. The calculations based on the theory of radiative transport can predict a different distribution of light within the medium. The differences in the forward model can directly influence the accuracy of the reconstruction. For example, if for a given distribution of optical properties, the diffusion model predicts a higher signal at a detector than actually measured, the reconstruction scheme can lower absorption and/or scattering coefficients in certain areas. In general the diffusion approximation is not as accurate when small sample geometries are considered in which source-detector separations are small and boundaries effects are dominant.

The transport theory can be more accurate when the medium contains regions in which the absorption coefficient is not much smaller than the scattering coefficient or when regions are considered in which the scattering and absorption are very low (so-called void-like regions), such as cerebrospinal-fluid-filled spaces in the brain, or the synovial-fluid-filled space in joints.

In order to determine whether there are any changes in the vasculature of the body part imaged or in the oxy and deoxy-hemoglobin or in the main protein in blood, a second set of transmission data and corresponding second set of images are generated after an external stimulus is applied to the imaged body part. The stimulus can be generated by applying an external pressure on the body part using a pressurizing device, such as but not limited to, a sphygmomanometer cuff placed around the body part. After the application of the stimulus, a second set of transmission data are taken and a second set of tomographic images are reconstructed using the same imaging and reconstruction methods as used for the generating of the first set of data and images.

Each set of transmission data and reconstructed images include information regarding optical properties (reflection, absorption, scattering) of the imaged body part. From these optical properties, parameters such as perfusion rates, oxy and deoxy hemoglobin concentrations, as well as blood volume can also be determined. By comparing the transmission data and the images in the first set with corresponding transmission data and images in the second set, biomarkers such as, but not limited to, distribution of optical properties, perfusion rates, and differences in oxy and deoxy hemoglobin concentrations can be ascertained. These biomarkers can then be used to differentiate between a sick and a healthy patient.

Multiple response characteristics can be defined that serve to discriminate healthy tissue from diseased tissue. For example, the minimum and maximum absorption coefficients, the ratio between the minimum and maximum absorption coefficients, the smallest and largest absorption and scattering coefficients, the ratios of these coefficients, and the variance of the absorption and scattering coefficients. Differences in these optically derived biomarkers can all be used individually or in combination to classify and monitor patients. For example, the absorption coefficient ($\mu_a$) decreases in patients with LEAD because of the decreased amount of blood flowing in the arteries, and thus the magnitude in the decrease of ($\mu_a$) may be proportional to the degree of the patient's LEAD. Further, the oxygenated hemoglobin trace may recover at a slower rate in patients with LEAD because the arteries may not be able to supply the oxygenated blood as quickly as patients with no occlusions in their arteries. The total hemoglobin concentration and total blood volume may also decrease for patients with LEAD because of the decrease in blood flowing through the arteries of the sick patients. Therefore, monitoring these biomarkers can enable the physicians to accurately diagnose the degree of PAD or LEAD by detecting the physiological change in the hemoglobin and the change in the optical properties of the vasculature with respect to the stimulus.

The image based biomarkers extracted from the first and second sets of optical tomography images can be used individually and in combination with other biomarkers to further increase the accuracy of the system in determining whether a patient is healthy or has PAD or LEAD. In addition, the results obtained using the tomographic imaging modalities as described above can also be used together with results obtained using other existing technologies to allow earlier and more appropriate intervention to treat this debilitating condition. For example, results obtained using ankle-brachial index (ABI) as well as that of Duplex Ultrasound scans, which are considered the standard techniques, can be used together with the results obtained using the tomographic imaging modality described above.

The data can also be reconstructed in order to obtain the differences in the metabolic activity in the joints, for example. By using data obtained using two wavelengths, the fluctuation in the oxygenated and deoxygenated hemoglobin concentrations for the finger joints can also be obtained. The spatial distribution of the f1lb021, [Hb] and [MT] in finger joints of healthy patients and patients with rheumatoid arthritis are markedly different. A ring structure is evident a healthy patient, a void-like center region shrinks until it is completely lost and the entire joint cavity is inflamed. A high metabolic rate activity can also be seen. Since the total hemoglobin concentration can be directly proportional to blood volume, this data can also be used to determine blood volume.

A similar protocol can be used to study the feet. Patients can have their ABI measured first, which is the ratio of the systolic pressure measured at the dorsalis pedis or posterior tibial artery to that of the brachial systolic pressure. Patients can place their foot inside the measuring module to target the major arteries of the foot. Then a pressure cuff can be placed around the patient's thigh. A baseline measurement can be taken and then pressure can be applied to the thigh until it constricts the venous return, while arteries can still be flowing blood to the lower extremities. The pressure can then be released for a rest period and then the cuff reapplied with stronger force to shut off both venous return and arterial supply. During the measurements, the patients can have multiple cuffs around their legs to compress the arteries.

The temporal response of the detector intensities can be used to reconstruct the data to obtain the spatial maps of the hemoglobin response of the foot cross sections that contain the dorsalis pedis and the posterior tibial artery. The same exemplary experiment can be repeated with a heated pad added at the measuring site in order to induce vasodilatation. The difference in the responses to the various stimuli can be used as signatures to diagnose LEAD in both diabetics and non-diabetic patients. The absorption coefficient ($\mu a$) may decrease in patients with LEAD because of the decreased amount of blood flowing in the arteries. The magnitude in the decrease of ($\mu a$) can be proportional to the degree of the patient's LEAD and these findings can be validated with the ABI measurements and ultrasound scan. The total hemoglobin concentration and total blood volume may also decrease for patients with LEAD because of the decrease in blood flowing through the arteries of the sick patients.

An alternative system that can be used is a frequency domain optical tomography system. This optical tomography system is capable of using high modulation frequencies up to 1 GHz, which allow for better separation of absorption and scattering and more accurate reconstructions.

To characterize the efficacy of optical tomography in identifying LEAD the sensitivity and specificity can also be determined. The results obtained can be compared with those of the ankle-brachial index (ABI) as well as that of Duplex Ultrasound. These are non-invasive diagnostic techniques that are currently used on patients suspected to have LEAD, before resorting to digital subtraction angiography. These diagnostic techniques can be used as standards, and differences in mean values and standard deviation of various optically derived classifiers that can be used to distinguish between diseased and healthy vasculature can be sought.

The ABI is a quantitative method for detecting lower extremity arterial disease. The optical images show different stages of LEAD. Table 1 shows the ABI measurements associated with mild, moderate and severe LEAD as well as those for patients with non-compressible arteries and healthy patients. One of the key advantages of optical tomography is that it is capable of imaging calcified arteries which are not diagnosable with ABI measurements.

TABLE 1

| Degree of LEAD | ABI |
|---|---|
| Healthy Control | 0.91-1.30 |
| Mild LEAD | 0.70-0.90 |
| Moderate LEAD | 0.41-0.69 |
| Severe LEAD/Critical Limb Ischemia | <0.4 |
| Non-compressible | >1.31 |

The other imaging modality that can be considered for comparison with optical tomography is Duplex ultrasound. Duplex ultrasound is commonly used in clinical settings to detect LEAD. Ultrasound however has a lot of operator dependent variables that affect its efficacy at detecting LEAD. In addition, ultrasound cannot provide reliable imaging if there are poor acoustic windows (e.g., bowel gas attenuation, diffuse vascular calcification, or metallic stents) or poor intrinsic echogenicity of the tissues. The ultrasound also only provides qualitative measurements which could vary in interpretation depending on the physician making the diagnosis. The ultrasound measurements can be grouped into 4 categories similar to the ABI measurements: healthy control, mild LEAD, moderate LEAD and severe LEAD. They can be compared with the optical tomography images of the same patients to determine the optical tomography imaging modality's sensitivity and specificity.

Several biomarkers can be acquired from optical tomography images taken during the clinical study and each parameter can be used individually and in combination with other biomarkers to determine if the patient has LEAD. To combine these biomarkers an analysis under a vector quantization based classification called Self-Organizing Mapping (SOM) can be used. SOM is an unsupervised learning method, with the purpose of transforming a feature vector of arbitrary dimension drawn from the given feature space into simplified generally 2D discrete maps. This method can allow producing multivariate receiver operating characteristic (ROC) curves from which sensitivity and specificities can be determined. Parameter combinations can lead to higher sensitivities when compared to single parameter classifications. The data can also be separated for patients with LEAD and those with LEAD and diabetes in order to examine if the biomarkers that maximize the accuracy of the diagnosis as defined by sensitivity and specificity.

Figure 11:
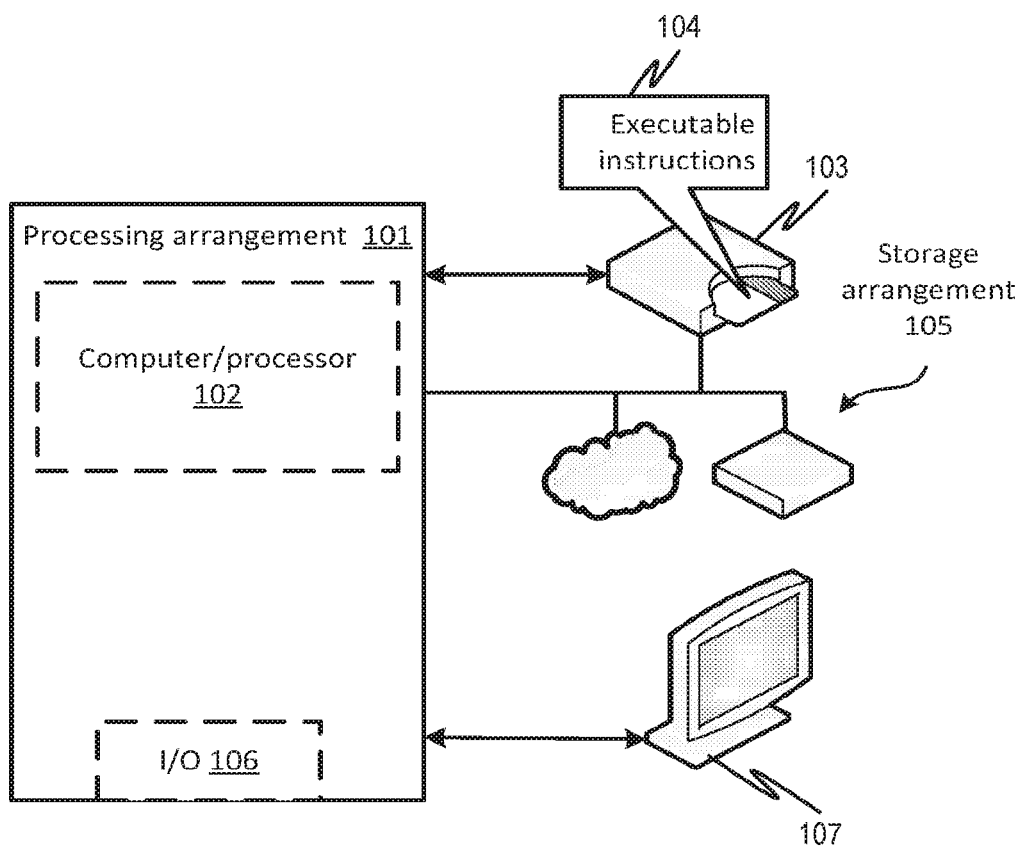
FIG. 11 shows an example of a computer processing system that can be used to implement the optical tomographic imaging methods described herein. The system is applicable to any of the embodiments described herein.

FIG. 11 shows an example of a computer processing system that can be used to implement the optical tomographic imaging methods described herein. For example, the imaging methods can be performed by a processing arrangement and/or a computing arrangement 101. Such processing/computing arrangement 101 can be, e.g., entirely or a part of, or include, but not limited to, a computer/processor 102 that can include, e.g., one or more microprocessors, and use instructions stored on a computer-accessible medium (e.g., RAM, ROM, hard drive, or other storage device).

A computer-accessible medium 103 (e.g., as described herein above, a storage device such as a hard disk, floppy disk, memory stick, CD-ROM, RAM, ROM, etc., or a collection thereof) can also be provided (e.g., in communication with the processing arrangement). The computer-accessible medium 103 can contain executable instructions 104 thereon. In addition or alternatively, a storage arrangement 105 can be provided separately from the computer-accessible medium 103, which can provide the instructions to the processing arrangement 101 so as to configure the processing arrangement to execute certain exemplary procedures, processes and methods, as described hereinabove, for example.

Further, the exemplary processing arrangement 101 can be provided with or include an input/output arrangement 106, which can include, e.g., a wired network, a wireless network, the internet, an intranet, a data collection probe, a sensor, etc. The exemplary processing arrangement 101 can be in communication with an exemplary display arrangement 107, which, according to certain exemplary embodiments of the present disclosure, can be a touch-screen configured for inputting information to the processing arrangement in addition to outputting information from the processing arrangement, for example. Further, the display and/or a storage arrangement can be used to display and/or store data in a user-accessible format and/or user-readable format.

Of special interest are the blood constituents oxy-hemoglobin (Hb02) and deoxy hemoglobin (Hb), which have distinctly different absorption spectra in the visible and near-infrared wavelength region. By performing measurements at multiple wavelengths, concentration of these chromophores as well as parameters such as total hemoglobin 11−1bT1=11−1b021+[Hb] or oxygensaturation St02=11−1b021/1HbT1 can be derived. Using advanced tomographic image reconstruction codes 2- and 3-dimensional maps of these and other parameters, such as blood volume, can be generated.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. In addition, all publications and references referred to can be incorporated herein by reference in their entireties. It should be understood that the exemplary procedures described herein can be stored on any computer accessible medium, including a hard drive, RAM, ROM, removable disks, CD-ROM, memory sticks, etc., and executed by a processing arrangement and/or computing arrangement which can be and/or include a hardware processors, microprocessor, mini, macro, mainframe, etc., including a plurality and/or combination thereof. In addition, certain terms used in the present disclosure, including the specification, drawings and claims thereof, can be used synonymously in certain instances, including, but not limited to, e.g., data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein, it can be explicitly being incorporated herein in its entirety. All publications referenced can be incorporated herein by reference in their entireties.

Many alternatives, modifications, and variations are enabled by the present disclosure. Features of the disclosed embodiments can be combined, rearranged, omitted, etc. within the scope of the invention to produce additional embodiments.

Furthermore, certain features of the disclosed embodiments may sometimes be used to advantage without a corresponding use of other features. Accordingly, Applicants intend to embrace all such alternatives, modifications, equivalents, and variations that are within the spirit and scope of the present disclosure.

While embodiments and applications of this invention have been shown and described, it would be apparent to those skilled in the art that many more modifications are possible without departing from the inventive concepts herein. The invention is not limited to the description of the embodiments contained herein, but rather is defined by the claims appended hereto and their equivalents. For example, the disclosed subject matter includes various structures and methods as applied principally to the problem of diagnosing or screening for vascular disease. However, the same may be applied to other types of diagnostic problems and/or body parts with relatively minor modification or no modification at all.

What is claimed is:

1. An optical tomography imaging system for detecting peripheral artery disease, comprising:
   an external body part stimulator that selectively applies a mechanical stimulus to a target body part to be inspected;
   an interfacing module arranged to contact the body part and image a portion of the body part using a plurality of light sources and a plurality of light detectors; and
   a controller programmed to
   control each of the plurality of light sources to emit light sequentially such that light is transmitted through the body part and transmitted light is detected by the plurality of light detectors,
   selectively activate the external body part stimulator to apply a first mechanical stimulus while acquiring a first series of time separated data from the light detected by the plurality of light detectors,
   subsequently selectively activate the external body part stimulator to apply a second mechanical stimulus while acquiring a second series of time separated data from the light detected by the plurality of light detectors,
   generate first cross sectional tomographic image data representing the body part based on the first series of time separated data, and generate second cross sectional tomographic image data representing the body part based on the second series of time separated data, and
   compare the first cross sectional tomographic image data to the second cross sectional tomographic image data.

2. The system of claim 1, wherein the external body part stimulator is a compression applicator.

3. The system of claim 2, wherein the external body part stimulator is a pressure cuff.

4. The system of claim 1, wherein the first cross sectional tomographic image data representing the body part and the second cross sectional tomographic image data representing the body part represent perfusion rates of blood.

5. The system of claim 1, wherein the first cross sectional tomographic image data representing the body part and the second cross sectional tomographic image data representing the body part represent hemoglobin concentrations.

6. The system of claim 1, wherein the first cross sectional tomographic image data representing the body part and the second cross sectional tomographic image data representing the body part represent volume of blood.

7. The system of claim 1, wherein the plurality of light sources are configured to emit near infrared light.

8. The system of claim 1, wherein the plurality of light sources are configured to emit selectable wavelengths and the controller is configured to emit different wavelengths simultaneously.

9. The system of claim 1, wherein the plurality of light sources and the plurality of light detectors include optical fibers.

10. The system of claim 9, wherein the optical fibers are in direct contact with the body part.

11. An optical tomography imaging method for detecting peripheral arterial disease in a body part of a subject, comprising:

introducing the body part into an interfacing module, the interfacing module including a plurality of light sources connected to light conduits, and a plurality of detectors connected to a plurality of light conduits, the interfacing module including a member shaped to enclose a portion of the body part, the plurality of light sources and the plurality of light detectors being detachably attached to the member so as to be positioned around the portion of the body part, the plurality of light sources and the plurality of light detectors being positioned on the member, wherein, in a first phase, each of the plurality of light sources sequentially emits light to be transmitted through the body part to be detected by the plurality of light detectors to generate a first set of light transmission data, wherein, in a second phase, each of the plurality of light sources sequentially emits light to be transmitted through the body part to be detected by the plurality of light detectors to generate a second set of light transmission data, wherein, in the first phase, the body part is exposed to a first external stimulus and during the second phase the body part is exposed to a second external stimulus or no stimulus;

reconstructing a first spatial distribution of a hemoglobin concentration in the body part based on the first set of light transmission data;

reconstructing a second spatial distribution of a hemoglobin concentration in the body part based on the second set of light transmission data; and comparing the first spatial distribution of a hemoglobin concentration to the second spatial distribution of a hemoglobin concentration.

12. The method of claim 11, wherein the first external stimulus includes pressure.

13. The method of claim 12, wherein the first and second sets of light transmission data includes light intensity data.

14. The method of claim 12, wherein the pressure is applied to the body part by inflating a pressure cuff attached to a limb to which the body part is attached.

15. The method of claim 14, wherein the pressure includes one of diastolic and systolic pressures.

16. The method of claim 11, further comprising differentiating between a sick and a healthy person based on a result of the comparing.

17. The system of claim 1, wherein the controller is further programmed to differentiate between a sick and a healthy person based on a result of the comparison between the first cross sectional tomographic image data and the second cross sectional tomographic image data.

* * * * *